US00PP35284P2

(12) United States Plant Patent
Elstgeest

(10) Patent No.: US PP35,284 P2
(45) Date of Patent: Jul. 25, 2023

(54) ***PHILODENDRON* PLANT NAMED 'PHELS02'**

(50) Latin Name: *Philodendron bipinnatifidum*
Varietal Denomination: PHELS02

(71) Applicant: Elstgeest Young Plants B.V., Rijsenhout (NL)

(72) Inventor: Debbie Elstgeest, Rijsenhout (NL)

(73) Assignee: Elstgeest Young Plants B.V., Rijsenhout (NL)

( * ) Notice: Subject to any disclaimer, the term of this patent is extended or adjusted under 35 U.S.C. 154(b) by 0 days.

(21) Appl. No.: 17/803,541

(22) Filed: Aug. 17, 2022

(30) Foreign Application Priority Data

Dec. 1, 2021 (QZ) ..... PBR 20213135

(51) Int. Cl.
*A01H 5/12* (2018.01)
*A01H 6/10* (2018.01)

(52) U.S. Cl.
USPC ..... Plt./381
CPC ..... *A01H 6/10* (2018.05)

(58) Field of Classification Search
USPC ..... Plt./381
CPC ..... A01H 6/10; A01H 5/12
See application file for complete search history.

*Primary Examiner* — Keith O. Robinson
(74) *Attorney, Agent, or Firm* — Samuel R. McCoy, Jr.

(57) ABSTRACT

'PHELS02' is a distinctive *Philodendron* plant which is characterized by dark green, glossy, pinnatifid leaves which are moderately concave and further exhibit foliar lobes that are strongly pendulous with strong, coarse undulation of the margins, as well as the uniformity and stability of these characteristics from generation to generation.

3 Drawing Sheets

Latin name of the genus and species: The Latin name of the genus and species of the novel variety disclosed herein is *Philodendron bipinnatifidum.*

Variety denomination: The inventive variety of *Philodendron* disclosed herein has been given the variety denomination 'PHELS02'.

BACKGROUND OF THE INVENTION

Parentage: 'PHELS02' is a spontaneous whole-plant mutation which was discovered growing amongst a cultivated population of *Philodendron bipinnatifidum* 'Hope ' plants (not patented) which was discovered by the inventor in September of 2019 at a commercial greenhouse in Rijsenhout, the Netherlands. The mutation was first noted for its unique, dark green leaves relative to those of the parent plant and was subsequently isolated for further evaluation in order to confirm the distinctness and stability of the characteristics first observed. Upon confirmation of distinctness and stability, the new *Philodendron* plant was selected for commercialization and given the name 'PHELS02'.

Asexual Reproduction: Asexual reproduction of the new cultivar 'PHELS02', by way of meristematic tissue culture micropropagation, was first initiated in March of 2020 at tissue culture laboratory in Rijsenhout, the Netherlands. Through seven subsequent generations, the unique features of this cultivar have proven to be stable and true to type.

SUMMARY OF THE INVENTION

The cultivar 'PHELS02' has not been observed under all possible environmental conditions. The phenotype may vary somewhat with variations in environment such as temperature, day length, and light intensity, without, however, any variance in genotype. The following traits have been repeatedly observed and are determined to be the unique characteristics of 'PHELS02'. These characteristics in combination distinguish 'PHELS02' as a new and distinct *Philodendron* cultivar:

1. *Philodendron* 'PHELS02' exhibits dark green, glossy, pinnatifid leaves; and
2. *Philodendron* 'PHELS02' exhibits moderately concave foliage with foliar lobes that are strongly pendulous.
3. *Philodendron* 'PHELS02' exhibits entire foliar margins with strong, coarse undulation.

BOTANICAL DESCRIPTION OF THE PLANT

Figure 1:
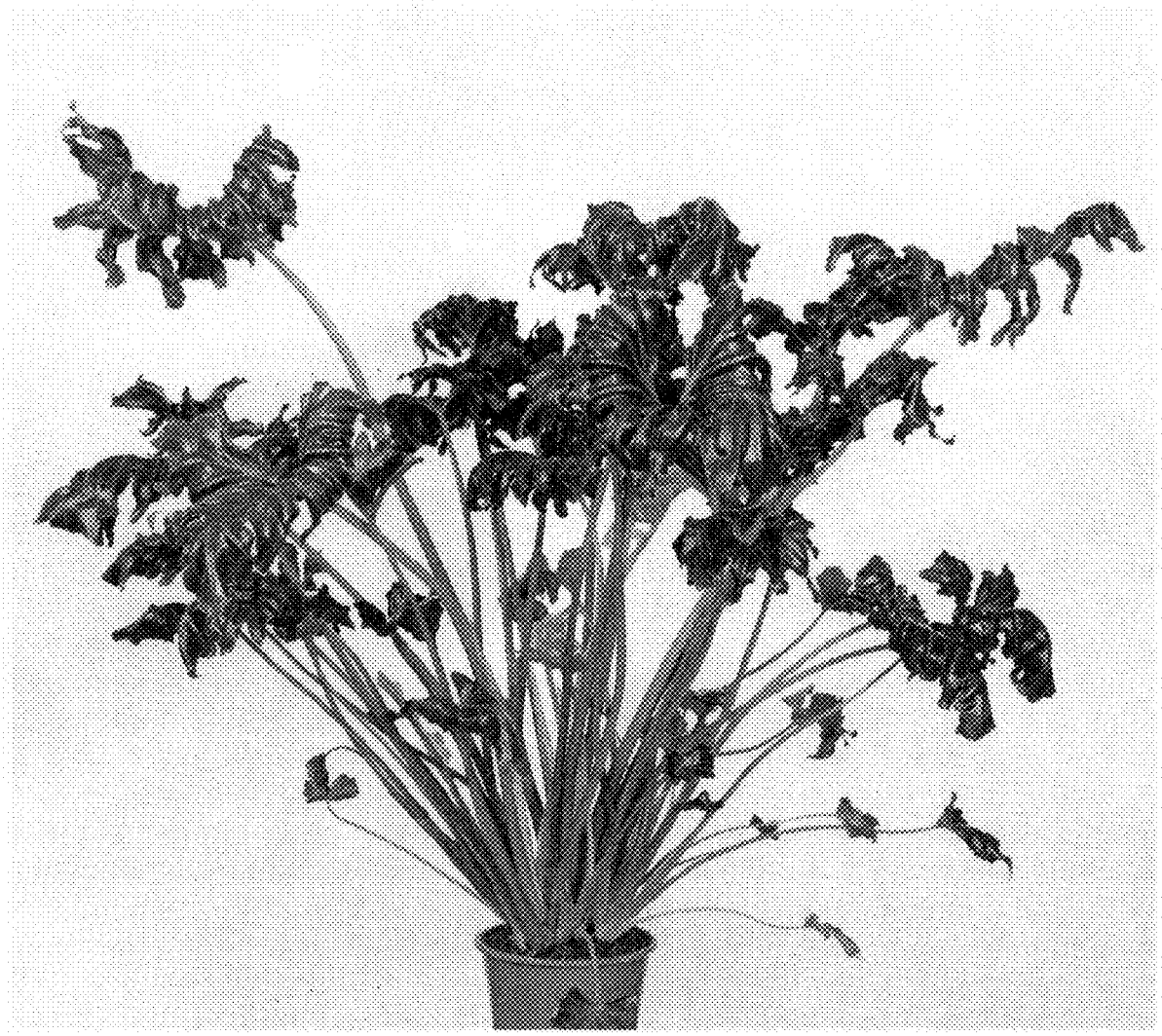
FIG. 1 illustrates, as nearly true as it is reasonably possible to make the same in color photographs of this type, an exemplary plant of 'PHELS02' grown in a commercial greenhouse in Rijsenhout, the Netherlands. This plant is approximately 12 months old, in a 13 cm container.
Figure 2:
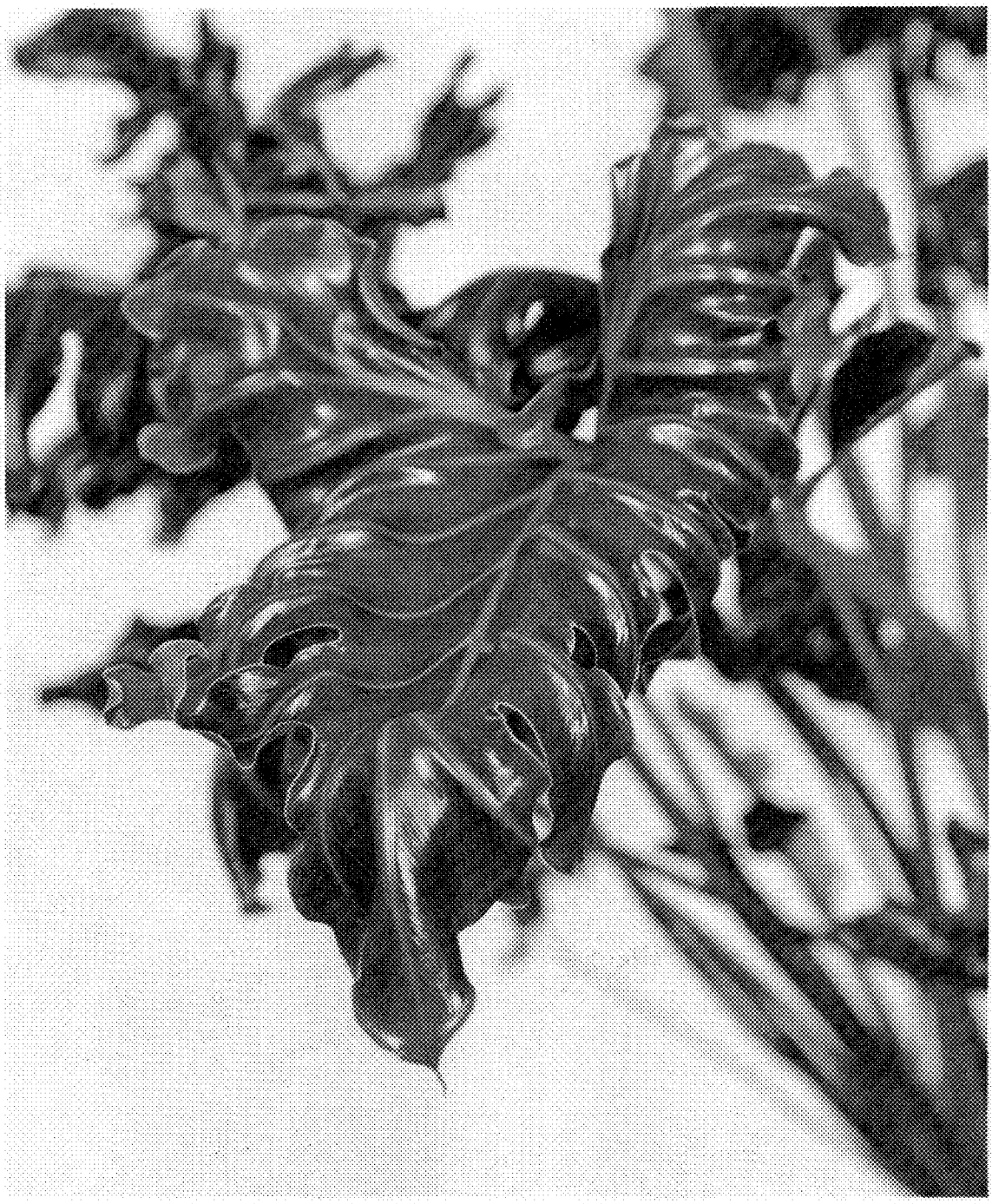
FIG. 2 illustrates, as nearly true as it is reasonably possible to make the same in color photographs of this type, the adaxial surface of the mature foliage of 'PHELS02'.
Figure 3:
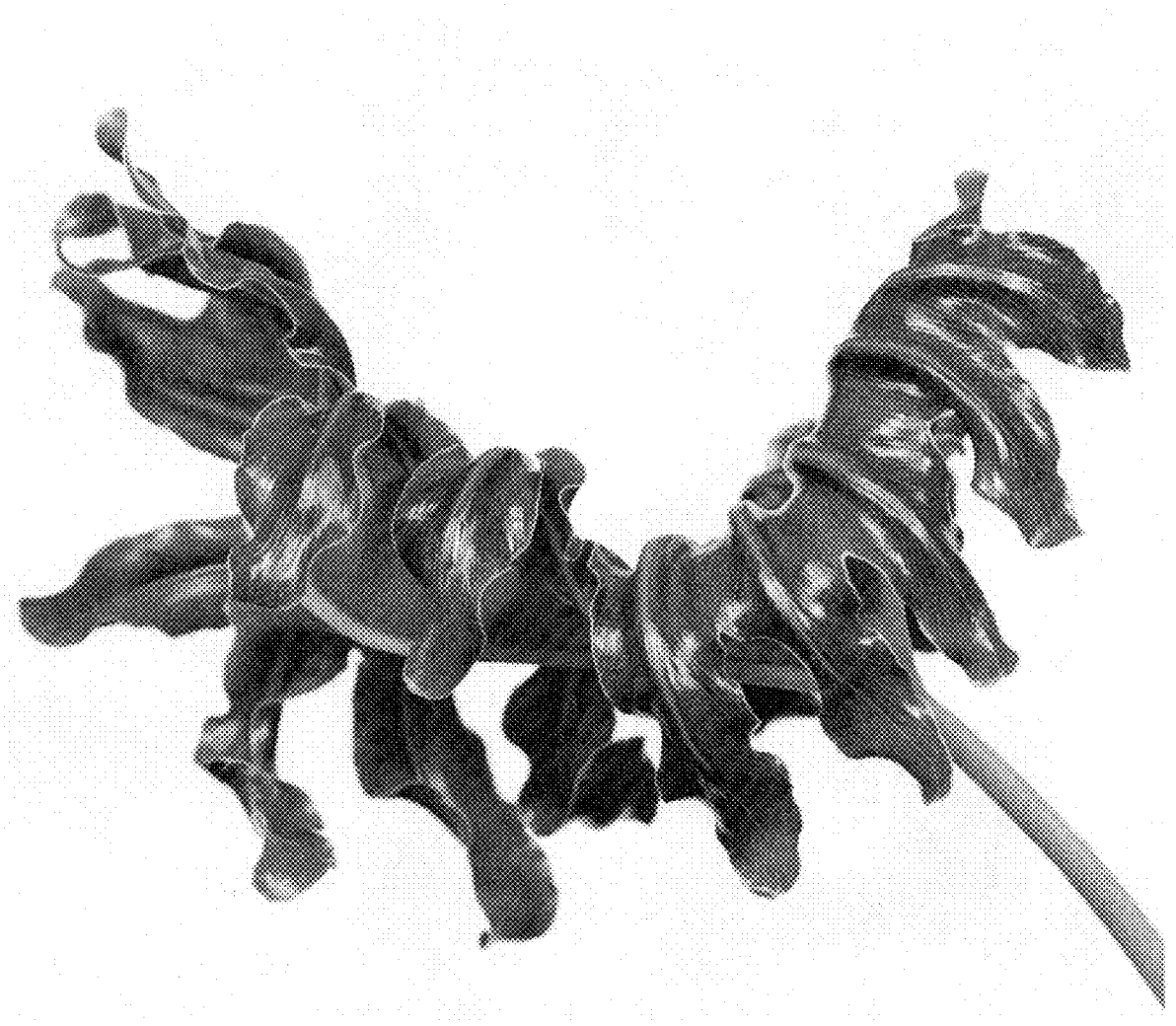
FIG. 3 illustrates, as nearly true as it is reasonably possible to make the same in color photographs of this type, the foliar lobes and abaxial foliar surface of 'PHELS02'.

The following observations and measurements, made in March of 2022, describe averages from a sample set of six 12-month-old 'PHELS02' plants grown in 13 cm nursery containers at a greenhouse in Rijsenhout, the Netherlands. Plants were produced using conventional greenhouse production protocols for *Philodendron* sp. which consisted of growing plants under shade, watering with drip irrigation, and producing plants without supplemental fertilizer, chemical pest measures, or photoperiodic treatments.

Those skilled in the art will appreciate that certain characteristics will vary with older or, conversely, with younger plants. 'PHELS02' has not been observed under all possible environmental conditions. Where dimensions, sizes, colors and other characteristics are given, it is to be understood that such characteristics are approximations or averages set forth as accurately as practicable. The phenotype of the variety may differ from the descriptions set forth herein with variations in environmental, climatic and cultural conditions. Color notations are based on *The Royal Horticultural Society Colour Chart*, The Royal Horticultural Society, London, 2015 (sixth edition).

A botanical description of 'PHELS02' and a comparison with the parent plant and most similar commercial cultivar are provided below.

Plant description:

*Growth habit*.—Broad spreading to upright herbaceous perennial with foliage growth from basal shoots.

*Plant shape*.—Broadly obovate to flattened globular.

*Height from soil level to top of foliar plane*.—58.5 cm.

*Plant spread*.—79.0 cm.

*Number of basal shoots per plant*.—7.

*Growth rate*.—Moderately fast to fast-growing.

*Plant vigor*.—Highly vigorous.

*Propagation*.—Type — Asexual propagation is accomplished by way of meristematic tissue culture micropropagation. Time to initiate rooting — Approximately 56 days at 21 degrees Celsius. Time to produce a rooted cutting — Approximately 16 weeks are needed to produce a marketable plant in a 14 cm nursery container.

*Disease and pest resistance or susceptibility*.—Neither susceptibility nor resistance to pests and diseases common to either *Philodendron bipinnatifidum* have been observed.

*Environmental tolerances*.—Adapt to temperatures as low as 5 degrees Celsius and at least as high as 40 degrees Celsius; moderate tolerance to rain; low to moderate tolerance to wind.

Roots:

*General*.—Moderately dense, moderately branched rooting; roots are fleshy and non-fibrous.

*Distribution in the soil profile*.—Shallow to moderately deep.

*Texture*.—Smooth, with fine lateral roots.

Foliage:

*Quantity*.—7 leaves per shoot.

*Arrangement*.—Alternate.

*Attachment*.—Petiolate.

*Division*.—Simple.

*Lamina*.—Shape — Broad ovate; lobed. Lobes — Apex — Obtuse. Depth of sinuses — Moderately deep. Sinus orientation — Parallel. Length — 18.2 cm, excluding the petiole. Width — 15.0 cm. Apex — Acuminate. Base — Very broadly cuneate to hastate. Aspect — Moderately concave; foliar lobes are strongly pendulous. Margins — Entire margins with strong, coarse undulation. Texture and luster, adaxial surface — Smooth, glabrous, and glossy. Texture and luster, abaxial surface — Smooth, glabrous, and moderately glossy. Color — Juvenile foliage, adaxial surface — Yellow-green, nearest to RHS 144A. Juvenile foliage, abaxial surface — Yellow-green, nearest to RHS 144A. Mature foliage, adaxial surface — Green, nearest to RHS 139A yet slightly darker. Mature foliage, abaxial surface — Nearest to a mixture of green and yellow-green, RHS 137B and 146A. Venation — Pattern — Pinnate. Color, adaxial surfaces — Green, nearest to RHS 137B. Color, abaxial surface — Yellow-green, nearest to RHS 150C.

*Petiole*.—Attitude — Upright and outward. Strength — Moderately strong. Aspect — D-shaped; adaxially flattened and abaxially rounded. Length — 50.0 cm. Width — 0.9 cm at the base and 0.7 cm at the point of attachment to the lamina. Texture and luster, adaxial surface — Smooth, glabrous and slightly glossy. Texture and luster, abaxial surface — Smooth, glabrous and, slightly glossy. Color, adaxial surface — Green, nearest to RHS 143A yet slightly darker. Color, abaxial surface — Green, nearest to RHS 143A yet slightly darker. Petiole wing — General — A thin flange of tissue, present at the base of petioles. Shape — Deltoid. Length — 12.7 cm. Width — 1.0 cm. Margin — Entire, with little to no undulation. Texture and luster — Smooth, glabrous and somewhat glossy. Adaxial color — Yellow-green, nearest to RHS 147D, and margined with a translucent greyed-green, nearest to RHS 192B. Abaxial color — Yellow-green, nearest to RHS 144B, and margined with a translucent greyed-green, nearest to RHS 192B; finely veined green, nearest to RHS 143A.

Inflorescence: To date, 'PHELS02' has not flowered.

COMPARISONS WITH THE PARENT PLANTS

Plants of the new cultivar 'PHELS02' differ from the parent, *Philodendron bipinnatifidum* 'Hope' (not patented), in the characteristics described in Table 1 below.

TABLE 1

| Characteristic | 'PHELS02' | 'Hope' |
|---|---|---|
| Foliage aspect. | Moderately concave; foliar lobes are strongly pendulous. | Carinate, margins slightly revolute. |
| Thickness of foliage. | Thicker than 'Hope'. | Thinner than 'PHELS02'. |
| General coloration of the foliage. | Darker green, relative to 'Hope'. | Lighter green, relative to 'PHELS02'. |

COMPARISONS WITH THE CLOSEST KNOWN COMPARATOR

Plants of the new cultivar 'PHELS02' differ from the closest known commercial comparator, *Philodendron bipinnatifidum* 'Winterbourn' (U.S. Plant Pat. No. 7,030), in the following characteristics described in Table 2 below.

TABLE 2

| Characteristic | 'PHELS02' | 'Winterbourn' |
|---|---|---|
| Foliage size. | Smaller than 'Winterbourn'. | Larger than 'PHELS02'. |
| Foliage shape; outline. | Broad ovate, with a broadly cuneate to hastate base and an acute apex with an acuminate apex. | Ovate to narrow-ovate, with the base often truncated and an acuminate apex. |

TABLE 2-continued

| Characteristic | 'PHELS02' | 'Winterbourn' |
|---|---|---|
| Foliage aspect. | Moderately concave; foliar lobes are strongly pendulous. | Nearly flat or slightly carinate, especially at the sinus, margins slightly revolute. |
| Foliar margin undulation. | Strong, coarse undulation. | Little to no undulation. |
| General coloration of the foliage. | Darker green, relative to 'Winterbourn'. | Lighter green, relative to 'PHELS02'. |

That which is claimed is:

1. A new and distinct variety of *Philodendron bipinnatifidum* plant named 'PHELS02', substantially as described and illustrated herein.

* * * * *